United States Patent [19]

Buchi

[11] 3,941,828

[45] Mar. 2, 1976

[54] PROCESS FOR THE PREPARATION OF CYCLIC KETONES

[75] Inventor: George Hermann Buchi, Cambridge, Mass.

[73] Assignee: Firmenich SA, Geneva, Switzerland

[22] Filed: May 21, 1974

[21] Appl. No.: 471,840

Related U.S. Application Data

[63] Continuation of Ser. No. 201,168, Nov. 22, 1971, abandoned.

[30] Foreign Application Priority Data

Dec. 9, 1970 Switzerland........................ 18303/70
Nov. 12, 1971 Switzerland........................ 16493/71

[52] U.S. Cl....... 260/468 K; 260/240 R; 260/514 K; 260/586 R; 260/586 C

[51] Int. Cl.$^2$.................. C07C 61/38; C07C 69/74
[58] Field of Search............ 260/468 K, 514 K, 586

[56] References Cited

OTHER PUBLICATIONS

Kende, Organic Reactions, 11, pp. 286–288, (1960).

*Primary Examiner*—Robert Gerstl
*Attorney, Agent, or Firm*—Pennie & Edmonds

[57] ABSTRACT

New process for the preparation of cyclic ketones possessing interesting organoleptic properties and including methyl 2-(cis-pent-2-enyl)-3-oxo-cyclopentylacetate and 3-methyl-2-(cis-pent-2-enyl)-cyclopent-2-enone, better known in the perfume industry as cis-methyl jasmonate and cis-jasmone respectively.

10 Claims, No Drawings

PROCESS FOR THE PREPARATION OF CYCLIC KETONES

This is a continuation of application Ser. No. 201,168, filed Nov. 22, 1971 now abandoned.

SUMMARY OF THE INVENTION

The present invention relates to a new process for the preparation of cyclic ketones having the formula

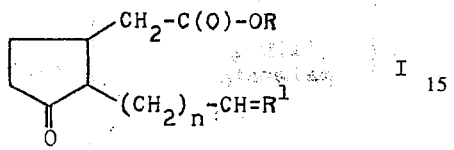

wherein the symbol $R^1$ represents an alkylidene radical containing one to 5 carbon atoms, R indicates a lower alkyl radical having a linear or a branched chain, and $n$ stands for the integer 0, 1, 3 or 4.

The invention also relates to a process for the preparation of compounds of formula

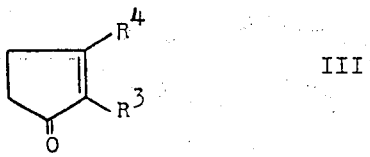

wherein $R^3$ represents either a lower alkyl radical comprising one to 6 carbon atoms, or an alkenyl or an alkynyl radical comprising 2 to 6 carbon atoms, and $R^4$ represents a lower alkyl radical or a hydrogen atom.

DESCRIPTION OF THE PREFERRED EMBODIMENTS

The compounds of formula I are fragrant substances which possess very particular olfactive properties either in a pure form or in admixtures with other perfume ingredients. When admixed with other odoriferous substances, these compounds develop powerful fragrant effects by exalting and rounding off the whole fragrance of the compositions in which they have been added, and by imparting fine and elegant notes to many perfumes.

More specifically, among the compounds having formula I, methyl 2-(cis-pent-2-enyl)-3-oxo-cyclopentylacetate, better known in the art of perfumery under the name of cis-methyl jasmonate, has a particular interest.

Said substance is a constituent of Jasminum grandiflorum L. and represents a valuable raw material in modern perfumery. Despite its importance its chemical synthesis has received little attention.

Early syntheses of methyl jasmonate have been reported in patent [U.S. Pat. No. 3,288,833] and in chemical literature [Helv. Chim. Acta, 45, 692 (1962)]. According to said processes, racemic methyl jasmonate was synthesized from racemic methyl 3-oxocyclopentane-1-acetate. The synthesis was structurally nonspecific and, as a consequence, the chosen route involved isomers separation via the corresponding semi-carbazones.

A more recent publication describes the synthesis of methyl jasmonate by another route, starting from methyl-2-oxo-cyclopentane-1-acetate [J. Org. Chem., 34, 2661 (1969)]. The preparation of methyl jasmonate by this latter method proceeds through intermediates which are difficult to separate from concomitantly formed isomers.

As a consequence, for both economical and practical reasons said syntheses have not found a suitable industrial application.

In accordance with the present invention, the process for the preparation of cyclic ketones having formula I, comprises
a. alkylating cyclohexane-1,3-dione by treating it with an alkyne halide of formula $$X-(CH_2)_n-C \equiv R^2 \qquad II$$

wherein X represents a halogen, $R^2$ represents an alkylidyne radical containing 1 to 5 carbon atoms, and $n$ stands for the integer 0, 1, 3 or 4;
b. reacting the obtained 2-alkynyl-cyclohexane-1,3-dione with a halogenating agent;
c. treating the resulting 2-halo-2-alkynyl-cyclohexane-1,3-dione with a mineral or an organic base, or an alkali metal salt acting as a base under the reaction conditions, for obtaining a 2-alkynyl-cyclopent-2-enone;
d. adding on to the cyclic double bond of the obtained ketone a dialkyl malonate in the presence of a base catalyst;
e. hydrolysing and subsequently decarboxylating the dialkyl 2-alkynyl-3-oxo-cyclopentyl malonate, obtained according to d), by treating it successively with a base and an acid;
f. esterifying the 2-alkynyl-3-oxo-cyclopentyl acetic acid obtained, and
g. partially hydrogenating the resulting ester in the presence of a partially poisoned hydrogenation catalyst.

The above synthesis has the great advantage of being structurally specific. By proceeding through specific positional isomers, the process of the present invention eliminates the expensive purification which was necessary whenever the synthetic routes disclosed in the prior art were applied.

A further advantage of the present invention is that of using as starting material cyclohexane-1,3-dione, which is a readily available, cheap commercial material.

For the preparation of the 2-halo-2-alkynyl-cyclohexane-1,3-dione, the reagents commonly known to produce positive halogens, such as, for instance, bromoacetamides, N-bromosuccinimide or tert.-butylhypochlorite can be used. This latter compound is preferred. The temperature at which the halogenation is carried out may be comprised in between about 0° and about –60° C, preferably comprised in between about –15° and about –20° C. The halogenation is preferably carried out by mixing the reagents in an inert organic solvent such as, for instance, an aliphatic, a cycloaliphatic or an aromatic hydrocarbon, or a chlorinated hydrocarbon, such as chloroform, dichloromethane, tetrachloroethylene. Chloroform is the preferred solvent.

For the preparation of the 2-alkynyl-cyclopent-2-one organic or mineral bases may be used. Suitable organic bases include tertiary amines, such as e.g. trimethylamine, triethylamine, N,N-diisopropylethylamine, pyridine, α-, β- or γ-collidine, ethyl pyridine, picoline or lutidine, and convenient mineral bases include alkali metal hydroxides, or alkali metal salts, such as sodium or potassium bicarbonate or carbonate. The reaction is preferably carried out in the presence of anhydrous sodium carbonate in suspension in an inert solvent. The commonly used solvents such as, for instance, lower alcohols, methyl-, ethyl- or isopropyl-alcohol, cyclic or acyclic hydrocarbons, aromatic or aliphatic hydrocarbons, ethers, such as tetrahydrofurane or dioxane, ester or amides, such as dimethylformamide, can be conveniently used. Anhydrous xylene or mesitylene are the preferred solvents.

The temperature at which the above mentioned reaction can be carried out is comprised in between about 15° and about 200° C. However, for practical reasons it is preferred to use a temperature which is near the boiling point of the chosen solvent. Said temperatures are not critical and temperature values above the boiling point of the chosen solvent may be used, namely by operating at a pressure higher than the atmospheric pressure.

The alkyl substituents of the dialkyl malonate used for the addition on to the double bond of the ring of 2-alkynyl-cyclopent-2-enone may be identical or different. In fact, suitable reagents include either dimethyl, diethyl, diisopropyl malonate, or mixed monalkyl-monotetrahydropyranyl malonates. By using these latter reagents the desired alkyl ester is directly obtained by partially saponifying the obtained addition compound under mild conditions and subsequently decarboxylating the resulting substituted malonic semi-ester.

The malonic diester addition is preferably carried out in the presence of a base catalyst. Sodium methoxide in alcohol solution is a preferred catalyst. Good yields of the addition product are obtained particularly when the reaction is carried out at temperatures comprised in between about 0° and −25° C.

The subsequent reactions of hydrolysis, decarboxylation and, as the case may be, esterification are carried out according to the usual practice. More specifically, it is preferred to obtain the ester derivatives of lower aliphatic alcohols in the presence of an acid catalyst, such as a strong mineral acid.

The partial hydrogenation of the triple bond of the resulting alkyl alkynyl-oxo-cyclopentyl acetate proceeds according to the techniques usually employed for selectively reducing an alkyne to an alkene. "Lindlar" type catalysts [Helv. Chim. Acta, 35, 446 (1952)], constituted by a palladium catalyst partially poisoned with quinoline or lead acetate, are conveniently used. Other methods commonly used for performing similar partial hydrogenations of triple bonds can also be used [see for example H.O. House, Modern Synthetic Reactions, W.A. Benjamin Inc.. New York (1965), p. 17 and following].

The alkyne halides of formula II may be prepared by usual methods [see for example Agr. Biol. Chem. (Tokyo), 30, 370 (1966)]. The chemical process described hereinabove can be illustrated by the following reaction pathway:

Pathway I

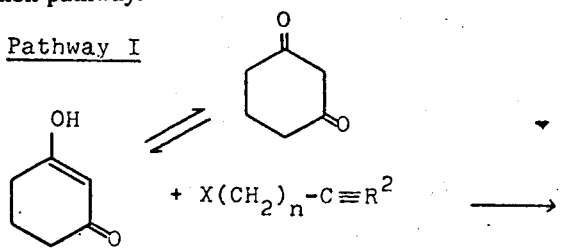

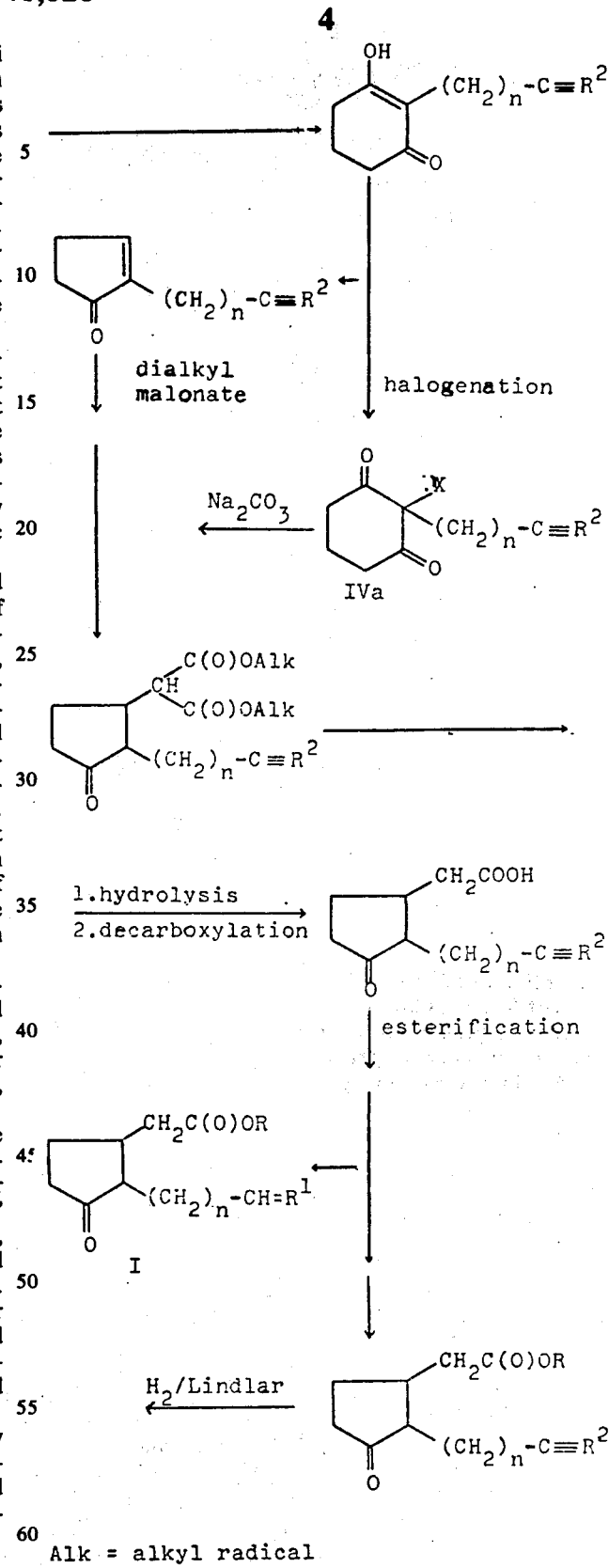

Alk = alkyl radical

In the above reaction pathway the symbols R, $R^1$, $R^2$ and X, and index n have the same meanings as those previously indicated for formulae I and II.

If a mixed mono-alkyl-monotetrahydropyranyl malonate is used instead of a dialkyl malonate, as shown hereinabove, the reaction pathway may be partially modified according to:

Pathway II

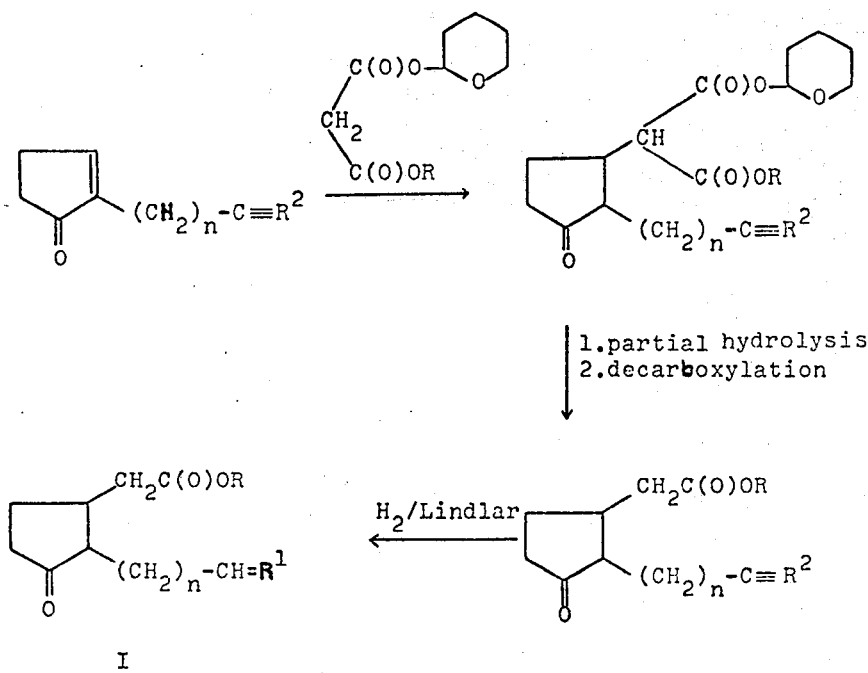

According to the above disclosed process, the compounds of formula I are obtained almost exclusively in the form of ethylenic isomers having the cis- structure.

The isomerisation of the cis- compounds to their corresponding trans- derivatives can be promoted by treating the cis-isomers with an acidic isomerisation agent according to usual methods.

Moreover, due to the presence of two asymmetric carbon atoms, ketones I can exist in the form of four cyclanic stereoisomers corresponding to two racemic compounds of formula I*a* and I*b*:

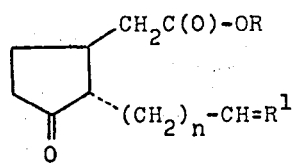 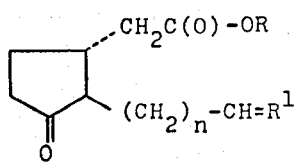

I*a*

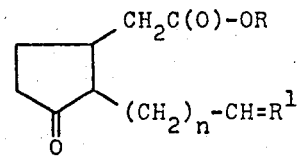 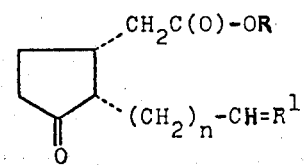

I*b*

The separation of the different isomers may be carried out by preparative vapour phase chromatography or by distillation by means of a spinning band column. However, for practical reasons the mixtures of the isomers directly obtained by the described process can be used as such in the perfume industry since the above-mentioned isomers possess similar olfactive properties.

The formation of a 2-alkynyl-cyclopent-2-enone according to one of the steps of the presently disclosed chemical process (see paragraph c) above described) proceeds by ring contraction of a 2-halo-2-alkynyl-cyclohexane-1,3-dione. Said reaction is novel and does not find analogy with previously known chemical processes. We have unexpectedly found that the ring contraction of 2-halo-2-alkynyl-cyclohexane-1,3-diones proceeds under relatively mild conditions.

Specific examples of the compounds which can be prepared according to the process of the present invention include: the lower alkyl esters of 2-(pent-1-enyl)-3-oxo-cyclopentyl acetic acid, 2-(pent-2-enyl)-3-oxo-cyclopentyl acetic acid, 2-(pent-4-enyl)-3-oxo-cyclopentyl acetic acid and 2-(3-methyl-but-2-enyl)-3-oxo-cyclopentyl acetic acid.

A specific embodiment of the present invention comprises:
a. alkylating cyclohexane-1,3-dione by treating it with 1-bromo-pent-2-yne in an alkaline aqueous medium;
b. treating a suspension of the resulting 2-(pent-2-ynyl)-cyclohexane-1,3-dione with a halogenating agent;
c. treating the resulting 2-halo-2-(pent-2-ynyl)-cyclohexane-1,3-dione with a mineral or an organic base, or an alkali metal salt acting as a base under the reaction conditions, for obtaining 2-(pent-2-ynyl)-cyclopent-2-enone;
d. adding on to the cyclic double bond of the obtained ketone a dialkyl malonate in the presence of a base catalyst;
e. hydrolysing and subsequently decarboxylating the dialkyl 2-(pent-2-ynyl)-3-oxo-cyclopentyl malonate, obtained according to d), by treating it successively with a base and an acid;
f. esterifying the 2-(pent-2-ynyl)-3-oxo-cyclopentyl acetic acid obtained and
g. partially hydrogenating the resulting ester in the presence of a partially poisoned hydrogenation catalyst to afford alkyl 2-(cis-pent-2-enyl)-3-oxo-cyclopentyl acetate.

A more specific embodiment of the present invention comprises:
a. alkylating cyclohexane-1,3-dione by treating it with 1-bromo-pent-2-yne in an alkaline aqueous medium and at a temperature comprised in between about 10° and about 60°C;
b. treating a suspension of the resulting 2-(pent-2-ynyl)-cyclohexane-1,3-dione in chloroform with tert.-butyl hypochlorite at a temperature comprised in between about −15° and −20°C;
c. treating a solution of the resulting 2-chloro-2-(pent-2-ynyl)-cyclohexane-1,3-dione in xylene with anhydrous sodium carbonate to yield 2-(pent-2-ynyl)-cyclopent-2-enone;
d. adding dimethyl malonate on to the ring double bond of the resulting ketone at a temperature of about −5°C and in the presence of sodium methoxide;
e. hydrolysing the resulting dialkyl 2-(pent-2-ynyl)-3-oxo-cyclopentyl malonate in aqueous alkaline medium at room temperature, and subsequently decarboxylating the acid thus obtained by means of sulfuric acid to yield 2-(pent-2-ynyl)-3-oxo-cyclopentyl acetic acid;
f. esterifying said acid by means of methyl alcohol in the presence of a mineral acid, and
g. partially hydrogenating the resulting methyl ester in the presence of a partially poisoned hydrogenation catalyst to yield methyl 2-(cis-pent-2-enyl)-3-oxo-cyclopentyl acetate.

According to the present invention a method for the preparation of the compounds of formula III comprises treating a compound of formula

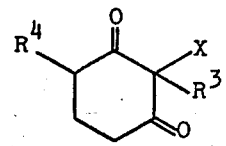

IV wherein X represents a halogen atom, and $R^3$ and $R^4$ have the same significance as that given for formula III, with either a mineral or an organic base, or an alkali metal salt acting as a base under the reaction conditions.

The compounds of formula IV used as starting materials in the above-mentioned process, can be prepared according to the same method as that described for the synthesis of the compounds having formula IVa — see pathway I. More specifically compounds IV may be prepared as follows:
a. 4-alkyl-cyclohexane-1,3-dione or, as the case may be, cyclohexane-1,3-dione, is alkylated by treating it with an alkyl-, alkenyl- or alkynyl-halide having the formula $R^3X$, wherein X represents a halogen atom and $R^3$ has the same meaning as indicated above, and
b. the resulting 2-alkyl-, 2-alkenyl- or 2-alkynyl-cyclohexane-1,3-dione is treated with a halogenating agent.

The halogenating agents which can be used in the above process include the reagents which give rise to the formation of positive halogens. The same reagents as those previously mentioned for the preparation of 2-halo-2-alkynyl-cyclohexane-1,3-dione are preferred.

The 4-alkyl-cyclohexane-1,3-diones, used as starting materials in the above defined preparation, can be obtained by hydrogenation of the corresponding hydroxylic aromatic derivatives [see for example: J. Chem. Soc., 103, 2033 (1913)].

4-Alkyl-cyclohexane-1,3-dione can also be prepared according to the method described in Zh. Obshch., Khim., 32, 3983 (1962) as reported in Chem. Abstr., 58, 13808 f. Said method can be summarized according to the hereinbelow given pathway.

Pathway III

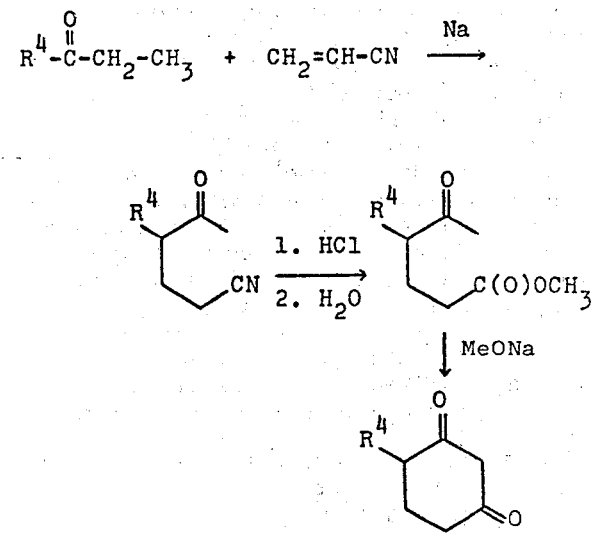

Specific examples of the compounds which can be prepared by the hereinabove disclosed process of the invention include 3-methyl-2-pentyl-, 3-methyl-2-(pent-2-enyl)- and 3-methyl-2-(pent-2-ynyl)-cyclopent-2-enone.

More specifically, the hereinabove disclosed process of the present invention enables the preparation of 3-methyl-2-(cis-pent-2-enyl)-cyclopent-2-enone ($R^3=$ cis-pent-2-enyl in formula III), 3-methyl-2-pentyl-cyclopent-2-enone ($R^3=$ pentyl in formula III), and of their homologues and isomers. The two above defined compounds are known in the art of perfumery as cis-jasmone and dihydrojasmone respectively and are characterized by their powerful and clinging scent.

A variety of synthetic processes for the preparation of cis-jasmone has been reported in the chemical literature but, so far, the synthesis of said compound has not found an industrial satisfactory solution. The first synthesis of jasmone has been realized by Treff and Werner already in 1935 starting from hex-3-enol [Ber., 68, 640 (1935)].

Most of the processes described afterwards comprise as a last step the cyclisation of undec-8-en-2,5-dione [see for example: J. Org. Chem., 31, 977 (1966); La France et ses Parfums, 12, 330 (1969); J. Chem. Soc. [C], 1024 (1969); Tetrahedron Letters, 1569 (1971); Tetrahedron Letters, 2575 (1971)].

This compound is rather difficult to synthesize and its formation proceeds via the hydrolysis of the corresponding furane derivative under strong acid conditions, as it is shown in French patent No. 1,592,859. Unfortunately the required acid conditions promote, parallel to the formation of the desired diketone, the formation of impurities which are then difficult to separate from the final compound.

The presently disclosed process proceeds via a new type of reaction and obviates to the above-mentioned disadvantages and enables the formation of the desired jasmone in good yield and in a pure form.

The formation of the compounds of formula III by the process of the present invention proceeds by ring contraction of a 4-substituted or unsubstituted 2-halo-2-alkynyl-, 2-alkenyl- or -2-alkyl-cyclohexane-1,3-dione in much the same way as that described above (see page 10).

Suitable organic bases include tertiary amines, such as for instance trimethylamine, triethylamine, N,N-diisopropylethylamine, pyridine, $\alpha$-, $\beta$- or $\gamma$-collidine, ethyl pyridine, picoline or lutidine, and convenient mineral bases include alkali metal hydroxides, or alkali metal salts such as sodium or potassium bicarbonate or carbonate. The reaction is preferably carried out in the presence of anhydrous sodium carbonate in suspension in an inert solvent. The commonly used solvents such as, for instance, lower alcohols, methyl-, ethyl- or iso-propyl-alcohol, cyclic or acyclic hydrocarbons, aromatic or aliphatic hydrocarbons, ethers such as tetrahydrofurane or dioxane, esters or amides, such as dimethylformamide, can be conveniently used. Anhydrous xylene or mesitylene are the preferred solvents.

As described above, the temperature for carrying out this reaction may vary in the range comprised in between about 15° and 200°C. However, for practical reasons it is preferred to use a temperature which is near the boiling point of the chosen solvent.

More specifically, the present process enables the formation of 3-methyl-2-pentyl-cyclopent-2-enone, 3-methyl-2-(pent-2-enyl)-cyclopent-2-enone and 3-methyl-2-(pent-2-ynyl)-cyclopent-2-enone respectively known under the names of dihydrojasmone, jasmone and dehydrojasmone.

In accordance to a modification of the above defined process cis-jasmone is obtained by using a 4-methyl-2-halo-2-(pent-2-ynyl)-cyclohexane-1,3-dione as starting material to yield dehydrojasmone which is then partially hydrogenated to cis-jasmone by using a partially poisoned hydrogenation catalyst of the Lindlar type (Helv. Chim. Acta, 35, 446 (1952) ).

According to the geometrical configuration of the ethylenic double bond of the alkenyl halides which are used as alkylating reagents in the above described process, the resulting 2-alkenyl-cyclopent-2-enones of formula III possess the cis- or trans- configuration. A further purification whenever necessary can be carried out by using the usual techniques of isomers separation such as fractional distillation or vapour phase chromatography.

The invention is further illustrated by the following examples, wherein the temperatures are indicated in degrees centigrade.

EXAMPLE 1

Preparation of 2-(pent-2-ynyl)-cyclopent-2-enone 2-chloro-2-(pent-2-ynyl)-cyclohexane-1,3-dione (80 g; 0.377 Mole) in dry xylene (800 ml) was allowed to reflux in the presence of anhydrous sodium carbonate (39.2 g; 0.38 Mole) until gas evolution ceased (12 h.). The reaction mixture was cooled, washed three times with water, and dried over magnesium sulfate, and the xylene was removed in vacuo. The resulting residue was distilled through a Vigreux column to afford 2-(pent-2-ynyl)-cyclopent-2-enone (41.3 g; 74 % yield), b.p. 67°–8°/0.01 Torr.

U.V. (EtOH) : 224 mμ ($\epsilon = 6600$);
IR : 3050, 1700, 1638, 1360, 1035, 1000, 790 cm$^{-1}$
NMR (CCl$_4$) : 1.13 (3H, $t$); 1.8–2.7 (6H, $m$); 2.9 (2H, $q$); 7.4 (1H, $m$) δ ppm
MS : M$^+$ = 148 (80); m/e: 133 (100); 91 (97); 148 (80); 105 (44.6); 39 (31.4); 77 (30); 51 (21.1); 65 (19.5); 119 (8).
$n_D^{20}$ = 1.5037.

The corresponding semicarbazone derivative had m.p = 204°–5°.

2-Chloro-2-(pent-2-ynyl)-cyclohexane-1,3-dione, used as starting material in the above described process, can be prepared as follows:

a. 2-(pent-2-ynyl)-cyclohexane-1,3-dione

1-Bromo-2-pentyne (100 g; 0.68 Mole), prepared according to the method described in Agr. Biol. Chem. (Tokyo) 30, 370 (1966), was added to a cold solution (0°–5°) of cyclohexane-1,3-dione (90 g; 0.8 Mole) and potassium hydroxide (56 g; 1 Mole) in 200 ml of water. The reaction mixture was stirred for 15 h. at room temperature and then 3 h. at 50°. The mixture was poured into a 4 N solution of sodium hydroxide (500 ml) and washed twice with ether for removal of the neutral compounds. The aqueous solution was acidified with a cold hydrochloric acid solution (400 g of concentrated HCl in 400 g of crushed ice). A precipitate was obtained which yielded after filtration, washing with water, and drying in vacuo 2-(pent-2-ynyl)-cyclohexane-1,3-dione; m.p. 162°–170°; 100 g (yield 82.5 %).

A small sample was crystallized twice from methanol; m.p. 179°–181°.

U.V. (EtOH) : 259 mμ ($\epsilon = 15{,}400$)
IR (CHCl$_3$) : 3330, 1620, 1180, 1130 cm$^{-1}$
NMR (CDCl$_3$) : 1.15 (3H, $t$); 1.8–2.6 (8H, $m$); 3.2 (2H unresolved, $q$); 8.3 (1H, $b$) δ ppm.

b. 2-Chloro-2(pent-2-ynyl)-cyclohexane-1,3-dione

Tert.-Butyl hypochlorite (108.5 g; 1 Mole) was added under a nitrogen atmosphere over a 2-hour period to a suspension of 2-(pent-2-ynyl)-cyclohexane-1,3-dione (178 g; 1 Mole) in dry chloroform (1.5 l) at −15° to −20°. After the addition was completed the reaction mixture was stirred for 2 h. at −15°. The solvents were removed under reduced pressure to afford the pure chloride.

Distillation through a small column over a few milligrams of sodium carbonate afforded pure 2-chloro-2-(pent-2-ynyl)-cyclohexane-1,3-dione; 162 g (76 %); b.p. 105°–7°/0.001 Torr. The product crystallized on cooling; m.p. 27°–9°.

IR (CHCl$_3$) : 1745, 1720, 1320, 1010 cm$^{-1}$
NMR (CDCl$_3$) : 1.05 (3H, $t$); 1.7–2.4 (4H, $m$); 2.4–3.4 (6H, $m$, complex band) δ ppm.

EXAMPLE 2

Preparation of methyl-2-(cis-pent-2-enyl)-3-oxo-cyclopentyl acetate a. dimethyl 2-(pent-2-ynyl)-3-oxo-cyclopentyl malonate 2-(pent-2-ynyl)-cyclopent-2-enone (59.2 g; 0.4 Mole), which was prepared according to the method described in Example 1, in dry methanol was added in a nitrogen atmosphere over a 0.5-h. period at −5° to a solution of dry methanol (200 ml), sodium metal (1.15 g; 0.05 Mole) and dimethyl malonate (66 g; 0.5 Mole). After the reaction mixture had been stirred for 1 hour at −5°, acetic acid (6g; 0.1 Mole) was added and the solvent removed under reduced pressure. Distillation through a small Vigreux column afforded the pure compound; b.p. 140°–5°/0.01 Torr; 107 g (95.5 %).
$n_D^{23}$ = 1.800
IR (liquid) : 3460, 1735, 1430, 1165 cm$^{-1}$
NMR (CCl$_4$) : 1.08 (3H, $t$); 1.5–2.5 (10 H, $m$); 3.65 (2H, $d$); 3.72 (6H, $s$) δ ppm
MS : M$^+$ = 280; m/e: 148 (100); 133 (48); 31 (42.8); 122 (36); 107 (26.3); 91 (23.4); 251 (17.7); 59 (17.1); 41 (16.6); 79 (16); 189 (7.4); 65 (6.3).

b. 2-(pent-2-ynyl)-3-oxo-cyclopentyl acetic acid

Sodium hydroxide (32 g; 0.8 Mole) dissolved in water (320 ml) was added slowly under a nitrogen atmosphere to the malonate derivative prepared according to paragraph a) hereinabove (107g; 0.382 Mole) at 15° over 3 h. The reaction mixture was stirred overnight at room temperature. After extraction with ether the aqueous layer was acidified with sulfuric acid (50 g; 0.5 Mole) in water (100 ml) and heated at reflux until gas evolution ceased (3–4 h.). After two extractions with ether, the organic layers were washed with water and dried over magnesium sulfate, and the solvent was removed under reduced pressure. Distillation through a small Vigreux column afforded the desired acid: 63.6 g (80 %); b.p. 155°–160°/0.01 Torr.
$n_D^{23}$ = 1.4895
IR (liquid) : 3460, 1735 cm$^{-1}$
NMR (CCl$_4$) : 1.09 (3H, $t$); 1.8–3.1 (10H, $m$); 8.6 (1H, $s$) δ ppm
MS : M$^+$ = 208; m/e: 122 (100); 107 (54); 179 (29); 79 (24.5); 91 (22.5); 41 (22.5); 55 (16.4); 133 (11.6); 149 (9.3); 67 (8.7); 193 (2.5).

c. methyl 2-(pent-2-ynyl)-3-oxo-cyclopentyl acetate

The acid prepared according to paragraph (b) hereinabove (63.6g; 0.306 Mole) and dry methanol (200 ml) in the presence of concentrated sulfuric acid (3 g) was heated at 40° for 3 h. The reaction mixture was cooled and sodium carbonate was added to it (5 g). The alcohol was removed under reduced pressure, the residue was extracted twice with ether, the organic layers were washed with water and dried over magnesium sulfate, and the solvent was then distilled off in vacuo. Distillation through a Vigreux column afforded pure methyl 2-(pent-2-ynyl)-3-oxo-cyclopentyl acetate: 63.5 g (93.5 %); b.p. 100°–103°/0.01 Torr.
$n_D^{23}$ = 1.4779
IR (liquid) : 3460, 1735 cm$^{-1}$
NMR (CCl$_4$) : 1.09 (3H, $t$); 1.7–2.9 (12H, $t$); 3.63 (3H, $s$) δ ppm
MS : M$^+$ = 222; m/e: 122 (100); 107 (52); 193 (43.3); 91 (25); 79 (23.6); 41 (21.2); 133 (16.7); 55 (16.7); 149 (13.8); 67 (8.4); 162 (2); 207 (0.75).

This compound gave a semicarbazone, m.p. 167°–9°.

d. methyl 2-(cis-pent-2-enyl)-3-oxo-cyclopentyl acetate

The acetylenic methyl ester obtained according to paragraph (c) hereinabove (63 g; 0.284 Mole) in petroleum ether (b.p. 50°–70°; 500 ml) was hydrogenated in the presence of a Lindlar type catalyst (1 g). After 3 h. 1 equivalent of H$_2$ had been absorbed. Filtration, removal of the petroleum ether under reduced pressure and distillation through a "Widmer" type column afforded the desired ester: 59.5 g (93.5 %); b.p. 88°–90°/0.01 Torr.
$n_D^{23}$ = 1.4720

IR (liquid) : 3450, 1735, 1690, 730 cm⁻¹

NMR (CCl₄) : 0.96 (3H, *t*); 1.7–2.7 (14H, *m*); 3.61 (3H, *s*); 5.25 (1H, *m*) δ ppm MS : M⁺ = 224; m/e: 83 (100); 151 (58); 41 (46.4); 224 (36); 95 (32.3); 55 (28); 109 (27.2); 67 (25.3); 193 (14.2); 133 (13.6); 121 (11.1); 206 (3.7); 177 (3.7); 167 (3.1).

EXAMPLE 3

Preparation of 3-methyl-2-(cis-pent-2-enyl)-cyclopent-2-enone a. 4-Methyl-2-chloro-2-(pent-2-ynyl)-cyclohexane-1,3-dione (3 g; 0.015 Mole) in dry xylene (15 ml) was allowed to reflux in the presence of anhydrous sodium carbonate (1.6 g; 0.015 Mole) until gas evolution ceased (3 h.). The reaction mixture was then washed with water, dried over magnesium sulfate and the solvent removed under reduced pressure. Distillation afforded 3-methyl-2-(pent-2-ynyl)-cyclopent-2-enone (dehydrojasmone); b.p. 80°–90°/0.001 Torr; 850 mg (35 %).

The purity of the above compound was 90 %; the remainder 10 % being 5-methyl-2-(pent-2-ynyl)-cyclopent-2-enone.

Dehydrojasmone showed the following spectral data:
IR (CCl₄) : 2205, 1700, 1650 cm⁻¹

NMR (CCl₄) : 1.07 (3H, *t*); 1.7–2.7 (9H, *m;* incl. 2.17: 3H, *s*); 2.91 (2H, *s*) δ ppm MS : m/e 162 (76); 147 (100); 133 (8.5); 119 (18); 105 (60); 91 (44).

b. Dehydrojasmone (260 mg; 0.016 Mole) in hexane (10 ml) was partially hydrogenated in the presence of a Lindlar type catalyst (10 mg). After 15 minutes 1 equivalent of H₂ had been absorbed. Filtration, removal of the hexane under reduced pressure and distillation of the resulting residue afforded a mixture (90–10) of 3-methyl-2-(cis-pent-2-enyl)-cyclopent-2-enone and 5-methyl-2-(cis-pent-2-enyl)-cyclopent-2-enone; b.p. 60°–70°/0.001 Torr; 250 mg (yield 95 %).

Further purification was achieved by vapour phase chromatography on a "CARBOWAX" 5 %, 2.5 m column at 175°.

IR (CHCl₃) : 1685, 1640 cm⁻¹

NMR (CCl₄) : 1.0 (3H, *t*, J=7 cps); 2.0 (3H, *s*); 2.1–2.6 (6H, *m*); 2.9 (2H, *d*, J=6 cps); 5.2 (2H, *m*) δ ppm 4-Methyl-2-chloro-2-(pent-2-ynyl)-cyclohexane-1,3-dione, used as starting material in the above described process, may be prepared as follows:

a. 4-methyl-cyclohexane-1,3-dione

This compound was prepared according to the method described in Zh. Obshch. Khim., 32, 3983 (1962) as reported in Chem. Abstr. 58, 13808 f. However, the cyclisation was run in benzene instead of methanol.

b. 4-methyl-2-(pent-2-ynyl)-cyclohexane-1,3-dione

1-Bromo-pent-2-yne (3.7 g; 0.025 Mole) was added to an ice cold solution of 4-methyl-cyclohexane-1,3-dione (3.12 g; 0.025 Mole) in potassium hydroxide (1.68 g; 0.030 Mole) and water (6 ml).

The reaction mixture was stirred for 15 h. at room temperature and then 12 h. at 50°. The mixture was poured into a 4N solution of sodium hydroxide (20 ml) and washed twice with ether for removal of the neutral compounds. The aqueous solution was acidified with cold hydrochloric acid solution (20 g of concentrated HCl in 20 g of crushed ice), and extracted with ether.

After removal of the solvent, distillation of the resulting residue afforded 4-methyl-2-(pent-2-ynyl)-cyclohexane-1,3-dione; b.p. 120°–140°/0.001 Torr; 3 g (65 %).
MS : 192 (64); 177 (100); 163 (215); 136 (17); 122 (31).

c. 4-methyl-2-chloro-2-(pent-2-ynyl)-cyclohexane-1,3-dione

Tert.-Butyl hypochlorite (1.66 g; 0.015 Mole) was added under a nitrogen atmosphere over a 15 minutes period to a solution of 4-methyl-2-(pent-2-ynyl)-cyclohexane-1,3-dione (2.88 g; 0.015 Mole) in dry chloroform (15 ml) at −15° to −20°. After the addition was completed the solvents were removed in vacuo to afford the crude chloride as a yellow oil; 3 g.

I claim:

1. A process for the preparation of cyclic ketones having the formula

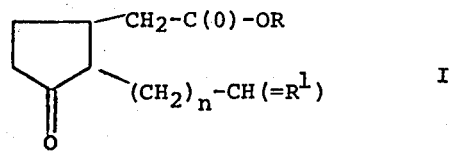

wherein the symbol (=R¹) represents an alkylidene radical containing one to five carbon atoms, R indicates a lower alkyl radical having a linear or a branched chain, and *n* stands for the integer 0, 1, 3 or 4, which comprises:

a. alkylating cyclohexane-1,3-dione by treating it with an alkyne halide of formula

wherein X represents a halogen, (≡R²) represents an alkylidyne radical containing one to five carbon atoms, and *n* stands for the integer 0, 1, 3 or 4;

b. reacting the obtained 2-alkynyl-cyclohexane-1,3-dione with a halogenating agent;

c. treating the resulting 2-halo-2-alkynyl-cyclohexane-1,3-dione in a solvent selected from the group of methyl-, ethyl-, and isopropyl alcohol, tetrahydrofurane, dioxane, dimethylformamide, anhydrous xylene and mesitylene, with a mineral or an organic base selected from the group of trimethylamine, triethylamine, N,N-diisopropylethylamine, pyridine, α-, β-, or γ- collidine, ethyl pyridine, picoline, lutidine, alkali metal hydroxides, and alkali metal carbonates and bicarbonates, at a temperature from about 15° to about 200°C, for obtaining a 2-alkynyl-cyclopent-2-enone;

d. adding on to the cyclic double bond of the obtained ketone a dialkyl malonate in the presence of a base catalyst;

e. hydrolysing and subsequently decarboxylating the dialkyl 2-alkynyl-3-oxo-cyclopentyl malonate, obtained according to (d), by treating it successively with a base and an acid;

f. esterifying the 2-alkynyl-3-oxo-cyclopentyl acetic acid obtained, and g. partially hydrogenating the resulting ester in the presence of a partially poisoned hydrogenation catalyst.

2. A process according to claim 1, wherein the halogenating reagent for preparing the 2-halo-2-alkynyl-cylohexane-1,3-dione is a compound acting as a positive halogen donor.

3. A process according to claim 1, wherein the positive halogen donor is tert.-butyl hypochlorite.

4. A process according to claim 1, wherein dimethyl malonate is added on to the ring double bond of 2-alkynyl-cyclopent-2-enone in the presence of sodium methoxide.

5. A process according to claim 1, which comprises:
a. alkylating cyclohexane-1, 3-dione by treating it with 1-bromo-pent-2-yne in an aqueous alkaline medium and at a temperature comprised in between about 10° and about 60°C;
b. treating a suspension of the resulting 2-(pen-2-ynyl)-cyclohexane-1, 3-dione in chloroform with tert.-butyl hypochlorite at a temperature comprised in between about −15° and −20°C;
c. treating a solution of the resulting 2-chloro-2-(pent-2-ynyl)-cyclohexane-1, 3-dione in xylene with anhydrous sodium carbonate, at a temperature from about 15° to about 200°C, to yield 2-(pent-2-ynyl)-cyclopent-2-enone;
d. adding dimethyl malonate on to the ring double bond of the resulting ketone at a temperature of about −5°C and in the presence of sodium methoxide;
e. hydrolysing the resulting 3-dimethoxycarbonyl-malonyl-2-(pent-2-ynyl)-cyclopentanone in an aqueous alkaline medium and at room temperature, and subsequently decarboxylating the acid thus obtained by means of sulfuric acid to yield 2-(pent-2-ynyl)-3-oxo-cyclopentyl acetic acid;
f. esterifying said acid by means of methyl alcohol in the presence of a mineral acid, and
g. hydrogenating the methyl ester in the presence of a partially poisoned hydrogenation catalyst to yield methyl 2-(cis-pent-2-enyl)-3-oxo-cyclopentyl acetate.

6. A process for the preparation of compounds of formula

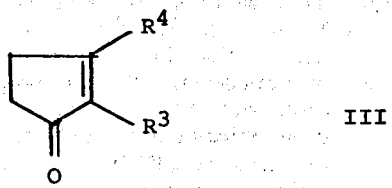

III wherein $R^3$ represents either a lower alkyl radical comprising 1 to 6 carbon atoms, or an alkenyl or an alkynyl radical comprising 2 to 6 carbon atoms, and $R^4$ represents a lower alkyl radical or a hydrogen atom, which comprises treating a compound of formula

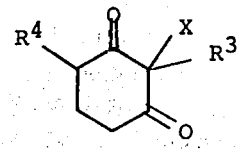

IV wherein X represents a halogen atom, and $R^3$ and $R^4$ have the same significance as that given above, in a solvent selected from the group of methyl-, ethyl-, and isopropyl alcohol, tetrahydrofurane, dioxane, dimethylformamide, and anhydrous xylene and mesitylene, with a mineral or an organic base selected from the group of trimethylamine, triethylamine, N,N-diisopropylethylamine, pyridine, α-, β-, or γ-collidine, ethyl pyridine, picoline, lutidine, alkali metal hydroxides, and alkali metal carbonates and bicarbonates, at a temperature from about 15° to about 200°C.

7. A process according to claim 6, wherein there is used a 4-methyl-2-halo-2-(cis-pent-2-enyl)-cyclohexane-1,3-dione as starting material to yield 3-methyl-2-(cis-pent-2-enyl)-cyclopent-2-enone.

8. A process according to claim 6, wherein there is used a 4-methyl-2-halo-2-pentyl-cyclohexane-1,3-dione as starting material to yield 3-methyl-2-pentyl-cyclopent-2-enone.

9. A process according to claim 6, wherein there is used a 4-methyl-2-halo-2-(pent-2-ynyl)-cyclohexane-1,3-dione as starting material to yield 3-methyl-2-(pent-2-ynyl)-cyclopent-2-enone.

10. A process according to claim 9, wherein the obtained 3-methyl-2-(pent-2-ynyl)-cyclopent-2-enone is partially hydrogenated in the presence of a partially poisoned hydrogenation catalyst to afford 3-methyl-2-(cis-pent-2-enyl)-cyclopent-2-enone.

* * * * *